United States Patent [19]
Vásquez

[11] Patent Number: 5,618,264
[45] Date of Patent: Apr. 8, 1997

[54] ABDUCTION MECHANICAL DEVICE FOR TREATMENT OF DISPLASIA OR CONGENITAL LUXATION OF THE HIP

[76] Inventor: Nectar D. Vásquez, Carrera 36 No. 3 Bis-08 Edifico, Elizabeth, Cali, (Valle), Colombia

[21] Appl. No.: 297,749

[22] Filed: Aug. 30, 1994

[51] Int. Cl.$^6$ ................................................. A61F 5/00
[52] U.S. Cl. ............................................. 602/24; 602/23
[58] Field of Search ............................. 602/5, 6, 23, 24

[56] References Cited

U.S. PATENT DOCUMENTS

| | | | |
|---|---|---|---|
| 2,935,984 | 5/1960 | Kerr | 602/24 |
| 3,114,368 | 12/1963 | Richmond | 602/24 |
| 3,834,376 | 9/1974 | Thum | 602/24 |
| 4,393,865 | 7/1983 | Lambert | 602/24 |
| 4,961,737 | 10/1990 | Orlando | 602/24 X |
| 4,964,858 | 10/1990 | Livny | 602/24 X |

FOREIGN PATENT DOCUMENTS 2174604  11/1986  United Kingdom ................ 602/24

*Primary Examiner*—Linda C. Dvorak
*Attorney, Agent, or Firm*—Beveridge, DeGrandi, Weilacher & Young, LLP

[57] ABSTRACT

An abduction device for treatment of dysplasia or congenital luxation of a femur hip in a newborn having a main body formed of a flexible material that has a front and rear edge portion spaced longitudinally, and a first and second side edge portion spaced laterally, the main body includes a plurality of sheaths which extend laterally between the side edge portions and in an intermediate area between the front and rear edge portions. Each of the sheaths has closed side boundaries, a closed lateral end boundary and an open lateral end. Slab members are received within the sheaths by insertion of a slab through an open end. The main body is received between the legs of the newborn, and the slabs are formed of a material that is sufficiently rigid to maintain the legs of the newborn separated to a desired extent. The open ends are arranged such that the slabs are accessible through the open ends for facilitating subsequent removal of the slabs following initial application of the device to the newborn. The device further includes a fastener assembly for releasably attaching the main body in position between the legs of the newborn. After an initial period of treatment, the slabs can be removed and shorter length slabs inserted such that the legs of the newborn are spread apart less than a maximum spacing utilized during the initial treatment period. The intermediate slab can be made shorter than the exterior slabs and an inclined end can be provided at each end of at least one exterior slab.

12 Claims, 2 Drawing Sheets

ABDUCTION MECHANICAL DEVICE FOR TREATMENT OF DISPLASIA OR CONGENITAL LUXATION OF THE HIP

FIELD OF THE INVENTION

The present invention is relented to apparatuses or mechanical devices for medical treatment of certain ailments. More precisely, the present invention is directed at a device for the treatment of dysplasia or congenital luxation in the hip of newborns. Consequently it is no a therapeutic treatment, but rather a simple mechanical device which might be used by the pediatrician or the mother under the direction of the pediatrician, to heal the malformation of the fetus during gestation, producing the luxation in the hip of the newborn.

BACKGROUND OF THE INVENTION

The coxo-femoral joint, commonly known as the hip, is a fundamental element of the human skeleton and must be in proper position in order for a person to have a harmonious walk and in order for a person to carry out normal physical activity both during childhood as well as during the whole life of the same. Because of its anatomical configuration and operation this joint must be considered one that is unique in the organism. It has two bony elements as follows:

1. A cup-shaped excavation known as the acetabulum which is designed to receive the second element described below.
2. The upper end of the femur, which is almost spherical, is known as the femoral head. For the proper functioning of the joint and so as not to produce friction between the two elements during walking, the depth of the "cups" muse be such that the sphere of the head is fully lodged and totally covered by the upper part of the "cup", known as the "acetabular roof"

The injuries in this joint, presently known indistinctly as C.L.H. (Congenital Luxation of the Hip) or C.D.H. (Congenital Dysplasia of the Hip)" constitute a serious health problem worldwide, not only among children but also with disastrous repercussions in adults.

There are two main types of joint injury. The first or "type 1" joint injury is an injury wherein the head definitely leaves the cup-shaped receptor. This type of luxation greatly depends on customs and traditions of people, with greater incidence in some social ambiances as compared to others. Certain local customs contribute to the luxation which tend to place the baby's femur in an inadequate position which propitiates the exit of the head from the acetabulum or pelvic cavity. An example of such a custom can be seen in the way the baby is wrapped in certain communities such as the Guambiano communities in Colombia where the baby is wrapped in a position tending to put together both femurs which position often results in the exit of the femur head from its pelvic cavity The second or "type II" joint injury is an injury wherein the femoral head remains within the firm acetabulumn; but since the "cup" lacks the ideal depth, the acetabular roof cannot cover completely the head. Given that the femoral head is within its "cup" and the joint is stable, no, pathological sign is appreciated when conducting a clinical examination. Thus this second type of injury is typically an asymptomatic type of injury, often going without being noticed until adult age, when, because of weight increase and natural wear of the joint, the injury produces pain which can be incapacitating. X-rays nevertheless show that the cause is coxo-artrosis. The treatment of this ailment in adults is complicated and difficult, since it supposes the total replacement of the hip with prosthesis which prosthesis must be operated upon whenever they come out of adjustment which occurs at variable intervals. Before the end of a five year period after surgery, 54% of people under 30 years of age who were subject to a total hip replacement are again subject to surgery because of maladjustments of the prosthesis. Complications that occur during his delicate surgery, presumed to take place each year with more frequency, has forced the initiation of the use of an orthopedic-robot, already patented, in order to carry out the bony cuts and couplings with more precision than the human hand. And the much more serious complications which arise during a total hip replacement procedure has led NASA to design a micro-transmitter, also already patented, in order to investigate the causes of the lack of adjustment. Not considering the surgical expenses, and the often less than satisfactory results of such procedures, the incapacities caused by artosis, which affect the U.S. payroll, is estimated to reach a total of $13 million a year. For Colombia even though reliable data is not available, the damages are similar. Consequently many countries, like Italy, are looking for a surgical correction of the problem among children.

The definitive optimum solution consists in an early diagnosis of the coxo-femoral injury in babies and dealing with it in an efficient and safe way with very low costs and complications. Nevertheless even in developed countries like the United States, England, Sweden, Italy, etc., more than 50% of children with Type I injuries, which injuries are afterwards verified by accident, are not diagnosed during the checkup done when they are newborn.

Only during the last years has the conclusion been reached that the much more frequent and serious repercussions on adults, who otherwise were previously thought to be free of a hip injury or hip problems, are due to coxo, femoral injuries considered "minimal" or not discovered upon a physical examination during infancy. Such minimal coxo-femoral injuries are present in X-rays taken during infancy, but because of the minimal nature of the deviation and the lack of appreciation of the potential adult ramifications were not recognized by the treating physicians, which is understandable since no one knew or suspected that the minimal joint injury would afterwards be the cause of irretrievable decay of the hip (coxo-artrosis).

During infancy and at the baby level, this type of injury might be successfully treated by a "physiological" method, without any hospitalization, only using the participation of the baby's mother. Presently, nevertheless, none of the conventional methods used worldwide for the treatment of cases, even those with early diagnosis are exempt of producing the death of the femoral head (avascular necrosis). This complication is so serious that if it is total, causes such a sever joint deterioration that the child would have preferred never having the luxation diagnosed.

The sensible way of diagnosing the injury, placing in evidence the joint pathology in the newborn, is described in the book by the applicant of the present invention named "CONGENITAL DYSPLASIA OF THE HIP-LOGICAL CONDUCT," Dr. Nectar Daza Vásquez 1986, Bogota, which is hereby included as reference.

The mechanical devices in the prior art designed for physiological treatment of said congenital malformation have as a general purpose the forcing of the femoral head inside the hip acetabulum. Since the bone system of the newborn is more cartilaginous than bony, the location and permanence of the femoral head within the acetabulm turns out to be relatively easy and it consolidates within a few days.

Actually, several mechanical devices are known for treatment in the newborn of the coxo-femoral injury, also known as dysplasia or congenital luxation of the hip.

The main devices are:

1. Fredjka's cushion
2. Von Rosen's splint; and
3. Pavlik's harness

In Fredjka's cushion, a rigid cushion is placed under the legs of the baby, so that they are separated and falling over ends of the cushion, while it is affixed to the baby's body by means of a breastplate hanging from the shoulders.

In Van Rosen's splint, a structure to be affixed to the baby's back is presented, while underneath appear clamps one for each leg, which keep the legs horizontally separated.

In Pavlik's harness, a harness component is affixed to the chest of the baby, while rigid straps, one for each leg, are laterally hung in order to separate the legs horizontally. In all three devices, the legs are horizontally spread so that the femoral head penetrates the acetabulum.

However, said devices have fixed dimensions which do not adapt well to the body of the baby during all of the treatment. Also given that the baby evolves quickly, all of the above devices tend to exert less separation between the legs of the infant, thus allowing a certain degree of undesirable movement between the femoral head and the acetabulum.

SUMMARY OF THE INVENTION

Therefore the main aim of the invention is to provide a mechanical device which keeps the legs of the baby horizontally separated, while making it possible to modify dimensions of the same so they will easily adapt to the evolution of treatment of the disease. Additionally, it is a main objective of the invention to provide a mechanical structure allowing for the separation of the baby's legs in several degrees, according to the specifications of the Doctor in each particular case.

The invention includes two strips or bands, generally rectangular, placed one above the, other, so that they both form free spaces or pockets in which rigid slabs, made of such materials as plastics or wood, are placed.

In the preferred embodiment of the invention, the chosen number of pockets is 3, each pocket lodging one rigid slab. Also, all of the slabs are substantially of the same length, even though they may vary in width, so several slab widths can be combined, so the device can be more adaptable to the baby.

In the preferred embodiment of the invention, three slabs are used, all 17 cm. long and they can be either of the same width or of different widths. Thus, generally speaking, the width of the central slab is of 6 to 7 cm., while the upper and lower slabs are generally 3 cm. Instead of the 6 to 7 cm. central slab, two 3 cm. width slabs or two 2 cm. width slabs can be placed. In this manner a device with a total of four (4) slabs can be constituted.

In another preferred mode, only two slabs are used. In another mode, more than four slabs are used. In this last case the device would approximate a small venetian blind with thin horizontal slabs.

All of these variations allow the pediatrician to adapt the device to the different conditions of the small patient, as well as the degree of development being reached, allowing in this manner the use of the same device throughout the whole treatment. This represents a great advantage over the rigid mechanical devices used up until now, whose dimensions were fixed and whose adaptability to different stages development was substantially impossible.

The device of the present invention is placed between the thighs of the baby so as to keep the legs open and separated, thus making it possible to keep he femoral heads in the desired location. The device has attachment means, which optionally can be two ribbons on each side of the upper part, in order to strap the device to the waist of the baby.

With the device, the hip of the newborn, originally injured or which could be injured, will stabilize at the latest in five days if it is kept permanently in its place. While the hip stabilizes, that is to say up to,the first control, each time the dirty fabric diaper placed between the device and the skin of the baby is changed, another person must keep the thighs open with his hands so that the femoral head remains in its place. Between the device and the skin of the baby there should be nothing more than a fabric diaper folded in the same manner and with the same dimensions of the device. Thus, the hard part of the abductor is in direct contact with the skin, directly applying the correct pressure on the affected joints.

The invention will be more clearly understood, when referring to the attached drawings, in which:

FIGS. 1A, 1B and 1C present known devices up to the present for treatment of dysplasia or congenital luxation of the hip in babies;

DETAILED DESCRIPTION OF THE PREFERRED EMBODIMENT

Figure 1A:
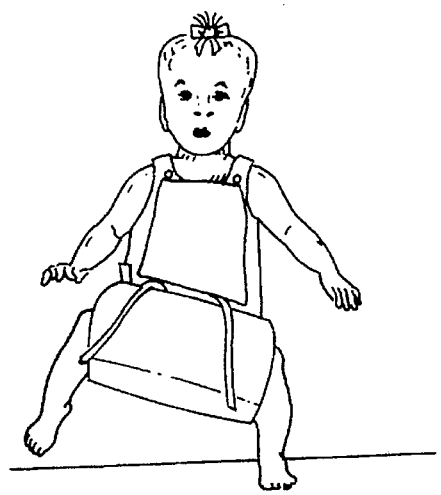
Figure 1B:
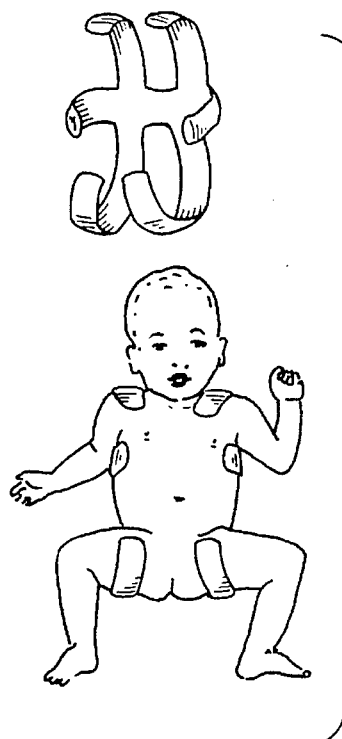
Figure 1C:
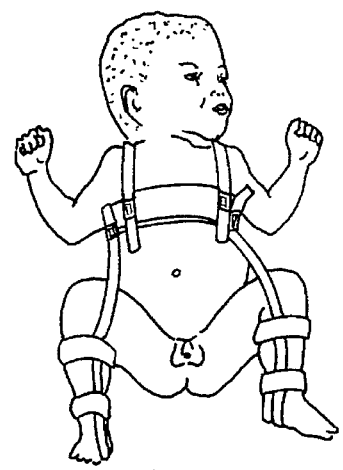

Referring to FIGS. 1A, 1B and 1C, there is illustrated in these figures the realizations of the prior art. FIG. 1A illustrates the Fredjka's cushion placed on an infant. As can be seen in the illustration, said cushion is a bulky element, soft, expensive and with unmodifyiable dimensions. Because it is bulky it tends to slip downward toward the knees. Because of this, and because it frequently is manufactured with a too soft structure, like a real pillow, it allows the baby to put together his knees, taking them to an adduction, injury creating position. The greatest percentage of failures in the reduction of injured hips on newborns is reported in the situations where the Fredjka's cushion has been used as the abductor device.

The term "adduction" means he position by which a limb or organ gets close to the middle pane imaginatively dividing the body in two symmetrical parts. With the term "abductor" there is indicated a device for supplying a position by which a limb or other organ is taken away from the middle plane which imaginatively divides the body in two symmetrical parts.

FIG. 1B illustrates the Von Rosen Splint. It is the prototype of the metal or plastic device, which, when placed behind the child by means of clamps, keeps the thighs open and separated. The inconvenience in this device is the excessive immobility in which the femoral head is kept.

Besides, if the femur head remains within its actabular "cup" the joint will stabilize within the first week of life after the birth of the newborn. Although further treatment is required, it is no longer necessary for the thighs to be opened to the maximum (maximum abduction) after this point. This maximum position is problematic since it is proven that it diminishes the blood flow towards the femoral head, possibly leading to the fearful avascular necrosis of the femoral head (death of the femoral head). Avascular necrosis is a complication so serious, that, if it is total, it causes such damage to the hip that the child would have preferred his ailment would have never been diagnosed. None of the conventional devices used today for treatment of congenital dysplasia of the hip is totally exempt from causing this complication (necrosis).

FIG. 1C illustrates the Pavlik harness. It is the most used apparatus worldwide for the treatment of the congenital dysplasia in the hip of the newborn. As can be see in FIG. 1C, it allows for flexing of the thighs with a moderate separation. With the Pavlik harness device, the hip has good mobility; but since it allows the thigh to get into adduction (an injury creating position), the femur head enters and leaves the acetabulum in a recurrent manner. Because of this, a significant number of failures have been reported in the attainment of a reduction in the number of injured heads, when using this device.

Figure 2:
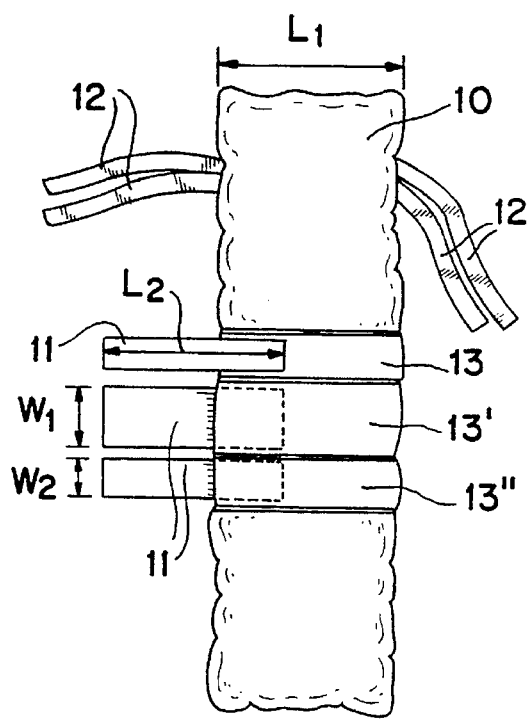
FIGS. 2 and 2A illustrate the new abduction mechanical device for the treatment of dysplasia or congenital luxation of the hip in babies.
Figure 2A:
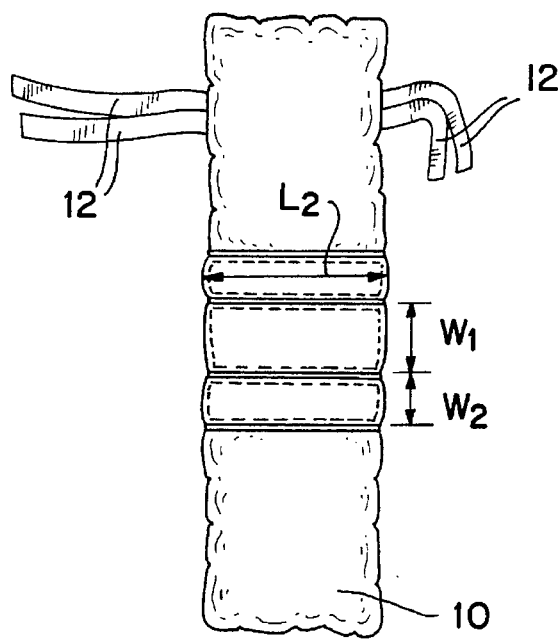

In FIGS. 2 and 2A there is illustrated the novel abductor device of the present invention. As can be seen in these illustrations, the device maintains the femoral heads permanently in their place, because of the following characteristics:

1. It is not bulky; on the contrary, it is thin and is easily maintained in a desired position between the legs of the newborn.
2. Its central zone has the necessary firmness and hardness in order to keep thighs separated and the femoral heads permanently in place, while not allowing the child to close his thighs placing the in the adduction injury creating position. In this manner it is possible that the hip, initially injured or potentially injured, stabilizes after five days of treatment.

Figure 3:
FIG. 3 illustrates a newborn using the device of the invention, after the first control, with the length of the separation slabs slightly shortened.
Figure 4:
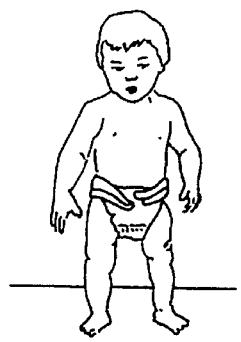
FIG. 4 shows an eight month old baby, in a standup position using the device of the invention already substantially shortened with legs substantially straightened.

With a stable hip, maximum abduction is no longer necessary. Consequently, the opening degree of the legs can and must be reduced in order to ease the blood flow in the femoral head. With this purpose, if the device of the invention has been in the treatment, it will be enough to shorten the slabs a few centimeters, as seen in FIGS. 3 and 4, in order to reduce the abduction degree.

The adaptability or dynamism of the device during the evolution of correction of the ailment is the most important characteristic of this apparatus. Since, in the beginning, the device allows satisfactory mobility. When the shortening of dimensions is initiated, the position in which the device maintains the hips is completely physiological and the mobility normal. The shortening of the dimensions can be easily carried out by the person in charge such as the mother or the physician, by means of a saw or a similar device. Also the slabs can be manufactured with weak areas, so small portions can be manually broken from the ends of the slabs.

The adaptability or dynamism of the device avoids the possibility that the treatment presents more complications than the disease itself that is to say the development of avascular necrosis of the femoral head. The possibility of an easy reduction of the abduction avoids maintaining the thighs of the baby exerting an exaggerated pressure on the femoral head against the acetabulum, thus favoring the blood flow in the femoral head.

As can be seen in FIGS. 2 and 2A, the novel abductor device consists in two elongated rectangular pieces 10 made of a soft and flexible material such a fabric, plastics, paper or similar material, which are joined at their common edges to form one piece leaving at the middle central zone free spaces 13 or strip like saddlebags, pockets or, compartments laterally open, through which slabs 11 can be introduced. Pieces 10 are shown as having lateral length L1 which is a preferred embodiment is 18 cm. Slabs 11 are preferably made of light wood, such as in thin plates, or made of rigid plastic or carton material.

In a preferred embodiment of the invention shown in FIGS. 2 and 2A, the central middle zone of piece 10 presents three superimposed saddlebags, with the first saddlebag 13 and the third saddlebag 13" of equal width, while the central saddlebag 13 is wider. The three saddlebags 13, 13' and 13" are of equal length. In the preferred model the length (L2) for all saddlebags is 17 cm., while the Width (W2) of the first and third saddlebags is approximately 3 cm. and the width (W1) of the central saddlebag is between 6 and 7 cm.

The slabs 11 made of wood, plastic or carton material and introduced into the three saddlebags, are rigid elements of substantially equal dimensions to those of the saddlebags. As can be seen in FIG. 2, the slabs ape laterally introduced inside the respective saddlebags, so each is substantially filled as can be seen in FIG. 2A. In place of the 6 to 7 cm. central slab, two 4 or 3 cm. slabs can be placed, so a 4slab device is constituted. The reduction of the width in the central slab possesses the advantage of facilitating the handling of the device between the legs of the baby, nevertheless maintaining the total initial separate of 17 cm. The saddlebags allow one to make adjustments in the number of slabs, so the invention can be an only two slab device or a device of more than four slabs, in order to have a better adaptability to the particular circumstances of a particular baby and/or the evolution of treatment of the malformation.

The device includes a fastener assembly preferably comprised of lateral strips 12 by which the device can be strapped to the waist of the child, as illustrated in FIG. 4. Equally, the slabs 11 can be shortened at the ends as the degree of dysplasia is reduced in the child. The shortening of the slabs thus reduces the degree of separation of the baby's legs. Such circumstance can also be appreciated in FIGS. 3 and 4, where it can be seen that the degree of separation of the legs has diminished considerably, up to the point that in FIG. 4, a baby in a standup position is shown with the device in place, after an eight month period of treatment has elapsed since his birth. It can be seen that the separation of the legs is already minimal and the device barely separates them. In FIG. 3 on the contrary, the baby is illustrated after the first control, and it can be seen that the device is substantially long and it provides sufficient separation of the baby's legs. The trend is to reduce the dimensions of the slabs and to modify its initial form in such manner so as to allow a normal motion development of the patient.

There has thus been describe and illustrated the invention without intending to limit the scope of the same to the phraseology and specific drawings presented for the purpose of illustration.

What is claimed is:

1. An abduction device for treatment of dysplasia or congenital luxation of a femur hip in a newborn, comprising:

a main body formed of a flexible material that has a front edge portion and a ear edge portion spaced longitudinally, and a first side edge portion and a second side edge portion spaced laterally, said main body further including a plurality of sheaths which extend laterally between said side edge portions and are positioned in an intermediate area between said front and rear edge portions, each of said sheaths'having closed side boundaries, a closed boundary at a first lateral end thereof, and an open end at a second lateral end thereof;

slab members which are dimensioned for containment within said sheaths, and said sheaths being sized for receiving a respective one of said slab members by insertion of said slab members through said open ends, said main body having a lateral width designed for receipt between the legs of the newborn, said slabs being formed of a material that is sufficiently rigid to maintain the legs of the newborn separated and said slabs being of a length which causes a femur head of the newborn to lodge within a hip acetabulum of the newborn, and said open ends being arranged such that sad slabs are accessible through said open ends formed in sad main body for facilitating subsequent removal following initial application of said device to the newborn; and a fastener assembly for releasably attaching the main body in the position between the legs of the newborn.

2. A device as recited in claim 1 wherein said main body is formed of a rectangular shape which is elongated longitudinally and said main body comprising three of said sheaths with each having the open end at a common one of said first and second side edge portions.

3. A device as recited in claim 1 wherein each of said sheaths shares at least one common side boundary.

4. A device as recited in claim 1 wherein an intermediate sheath, longitudinally positioned between two other sheaths, is of a greater longitudinal width than said two other sheaths.

5. A device as recited in claim 1 wherein there are a total of three sheaths with a longitudinally intermediate sheath having a width greater than two longitudinally exterior sheaths.

6. A device as recited in claim 5 wherein said sheaths and slabs each have a lateral length of about 17 cm and said intermediate sheath and corresponding slab having a longitudinal width of about 6 to 7 cm and said exterior sheaths and slabs received therein having a lateral length of about 17 cm and a longitudinal width of about 3 cm.

7. A device as recited in claim 1 wherein at least one of said slabs has means for facilitating a reduction in lateral size for providing for a reduction in leg separation following an earlier period of treatment.

8. A device as recited in claim 7 wherein said means for facilitating a reduction in lateral size includes a weakened area formed in said at least one slab.

9. A device as recited in claim 1 wherein said slab is formed of a wood material.

10. A device as recited in claim 1 wherein there are a total of four sheaths each with an open end positioned essentially commensurate with one of said side edge portions of said main body.

11. A device as recited in claim 1 wherein said fastener assembly includes a pair of longitudinally spaced apart straps that extend out from said main body in a lateral direction.

12. A device as recited in claim 1 wherein said open ends are uncovered during use of said device.

* * * * *